United States Patent [19]
Luckman

[11] Patent Number: 5,520,695
[45] Date of Patent: May 28, 1996

[54] INSTRUMENTS FOR USE IN KNEE REPLACEMENT SURGERY

[75] Inventor: Thomas Luckman, East Falmouth, Mass.

[73] Assignee: Johnson & Johnson Professional, Inc., Raynham, Mass.

[21] Appl. No.: 242,945

[22] Filed: May 16, 1994

Related U.S. Application Data

[62] Division of Ser. No. 837,306, Feb. 14, 1992, abandoned.
[51] Int. Cl.$^6$ .................................................. A61B 17/56
[52] U.S. Cl. .............................. 606/88; 606/79; 606/82; 606/96
[58] Field of Search .................... 606/79, 82, 86–90, 606/96; 128/898

[56] References Cited

U.S. PATENT DOCUMENTS

| | | | |
|---|---|---|---|
| 4,787,383 | 11/1988 | Kenna | 606/88 |
| 5,116,338 | 5/1992 | Poggie et al. | 606/90 |
| 5,122,144 | 6/1992 | Bert et al. | 606/87 X |
| 5,304,181 | 4/1994 | Caspari et al. | 606/88 X |
| 5,314,482 | 5/1994 | Goodfellow et al. | 606/88 X |

FOREIGN PATENT DOCUMENTS

| | | | |
|---|---|---|---|
| 0104732 | 4/1984 | European Pat. Off. | 606/88 |

OTHER PUBLICATIONS

New Jersey Tricompartmental Total Knee System, Surgical Procedure by Frederick Buechel, DePuy, 606/88 1984.
Knee Replacement Using the Insall/Burstein Total Knee Condyla Knee System, Insall & Burstein, N. Y. Society for RRC.
Zimmer Intramedullary Knee Instrumentation for the Miller/Galante Total Knee System, Zimmer Inc.

*Primary Examiner*—Mickey Yu
*Assistant Examiner*—Brian E. Hanlon
*Attorney, Agent, or Firm*—Joseph F. Shirtz

[57] ABSTRACT

The present invention relates to an instrument and method for performing a partial knee replacement and, in particular, a single condyle replacement method. The instrument includes a tibial mounted platform which has formed thereon a keyed slot for receiving a spacer which spacer is positioned between the femur and tibia of the knee joint being replaced. The spacer receives thereon a positioning element which positioning element includes guides for guiding a drill to drill mounting holes for mounting further instruments used in the knee operation. In particular, the mounting holes are drilled when the femur and tibia are in a predetermined angular relationship with the spacer providing a predetermined spacial relationship. In this way, the mounting holes are properly determined and positioned with respect to the relationship between the femur and tibia. A saw guide is mounted to the mounting holes and used to guide a saw when cutting the anterior chamfer, the posterior chamfer and the posterior femoral cut. A further drill guide is then mounted to the mounting holes after removal of the saw guide for drilling holes for receiving the lugs of the condyle prosthesis.

3 Claims, 7 Drawing Sheets

INSTRUMENTS FOR USE IN KNEE REPLACEMENT SURGERY

This is a division of application Ser. No. 07/837,306 filed Feb. 14, 1992, now abandoned which is hereby incorporated by reference.

FIELD OF THE INVENTION

This invention relates to surgical instruments and, in particular, to instruments for use in preparing the bones of a joint for receiving prosthesis.

BACKGROUND OF THE INVENTION

In total knee replacement surgery, it is known to use instrumentation to guide the cuts made to the proximal tibia and the distal femur in order to properly align the cuts with the bone.

For example, U.S. Pat. No. 4,524,766 describes a system of precision instruments for utilization in knee surgery. The instrumentation provides a series of alignment and cutting guides which function to align the various necessary cuts of the bone structure with respect to the various body parts. FIG. 7 of that reference as well as FIG. 15 shows certain interrelational instrumentation used in aligning the cuts, in particular, the distal femur cut and the proximal tibia cut.

U.S. Pat. No. 4,938,762 refers to a reference system for implantation of condylar total knee prostheses. This device involves a cumbersome set of reference systems used for total knee prostheses which comprises a measuring rod which is parallel to the longitudinal axis of the tibia which has a pair of attachment arms for attachment to the tibia. A guide rail is connected to the measuring rod having a scale thereon and an adjustable measuring carriage to which a cutting block for performing the necessary osteotomies is affixed for movement in two directions. Of particular interest with respect to the present application is FIG. 2 of that reference and the accompanying text.

U.S. Pat. No. 4,574,794 is entitled, "Orthopaedic Bone Cutting Jig and Alignment Device". This device constitutes a large cumbersome frame which attaches to the lower extremity of the leg and adjusts for the alignment of the various bone cuts.

U.S. Pat. No. 4,421,112 describes a tibial osteotomy guide assembly and method. That reference is described as having a method and guide assembly for use in tibial osteotomy wherein two pairs of guide pins are inserted into the tibia at predetermined angles with respect to each other through a guide block. The adjacent surfaces of the pairs of pins are then used to precisely guide a saw by which a wedged shape segment of the tibia is removed.

U.S. Pat. No. 4,487,203 entitled, "Tri-Planer Knee Resection Method" describes as apparatus for use in a tri-planer knee system which includes a single guide member for use in resecting the distal femur condyles, the proximal tibia and the distal femur. The instrumentation includes femur and tibia guide rods, a tibia adapter, a tibia bar and a femur bar for establishing equal flexion and extension gaps in tri-planer resection.

U.S. Pat. No. 4,567,885 entitled, "Tri-Planer Knee Resection System" describes a tri-planer knee resection system which is provided for preparing a knee joint for a prosthesis. This patent matured from an application which was a division of the application which matured into the '203 patent above.

U.S. Pat. No. 4,722,330 entitled, "Femoral Surface Shaping Guide for Knee Implants" describes a guide for mounting on an intermedullary alignment guide which references the central long axis of the femur in shaping the distal femoral surface and a method for shaping the distal femur using the shaping guide.

U.S. Pat. No. 4,892,093 entitled, "Femoral Cutting Guide" describes a cutting guide which is used for guiding a saw blade during the preparation of a femur for the implant of the femoral component of a knee prosthesis. The guide includes guide surfaces for enabling the cutting of all four of the anterial femoral cut, the posterial femoral cut, the anterior chamfer and the posterior chamfer, while the cutting guide remains located and secured to the femur in a single position.

U.S. Pat. No. 4,926,847 entitled, "Surgical Cutting Block" issued previously to the present inventor. That device provided a significant advance in the development of cut saw guides for knee surgery and provided a cutting guide to position a bone cutting device. The cutting guide has at least one fixed or stationary surface and a movable surface to create a slot or gap between the fixed surface and the movable surface. The cutting device is positioned and held in the slot to make accurate bone cuts.

While the above-described devices have provided mixed results in the advancement of the surgical technique in total knee prostheses replacement, it has been found that when doing less radical single condyle replacement that the interrelationship between the two surfaces, that is the proximal tibial surface and the distal femur surfaces, is difficult to align. That is, in a single condyle replacement, the remaining healthy condyle is left in tact as well as the receiving tibial tray on the proximal tibia. Only the diseased portion of the single condyle is removed. Thus the new condyle prosthesis must be aligned not only with the reference to the mechanical axis of the patient but also with respect to the condyle which remains in tact and unchanged by the surgery.

SUMMARY OF THE INVENTION

The present invention, therefore, provides a unique set of instruments which provide an interrelationship between the femur and the tibia such that the cut on the proximal tibia is related to the cuts made on the femur for the reception of the prosthesis. Thus, the alignment between the two bones is established by the instrumentation in order to more closely match the operation of the condyle which has been removed.

The invention provides for an instrument for use in surgical joint replacement for replacing an articulating joint between a first skeletal member and a second skeletal member. The instrument comprises a first skeletal member mountable platform which is positioned in a predetermined position relative to the first skeletal member. A skeletal member positioner which has a face is mounted to the platform for medial-lateral and posterior-anterior adjustment and positionable in relative mating position between the face of the positioner and the first skeletal member. In this way, the face which is angularly fixed with respect to the platform is used to position the second skeletal member in a predetermined angular relationship to the first skeletal member. This relationship includes both rotational and angular positioning.

The positioner may include a spacer which is received by the platform in order to fix the relative displacement between the two skeletal members. The spacer may be positionable along a surface of one of the skeletal members and used to physically place the second skeletal member.

The positioner may be movable in two linear directions both posterior-anterior and medial-lateral. In this way, the positioner can be adjusted relative to the first cut so that it places the other skeletal member in the proper position. This permits minor adjustment of the positioner relative to the actual physical make-up of the joint being replaced.

Once the two skeletal members are in appropriate relationship, both spacially and angularly, the positioner provides a guide for boring mounting holes in the first skeletal member. These mounting holes are later used for mounting a saw guide for making one or more remaining cuts to the first skeletal member. This fixes the position of the one or more later cuts relative to the second skeletal member such that the cuts are made in a predetermined position on the first skeletal member and in known relationship to the second skeletal member. Thus, when the prosthesis is eventually added to the space formed by the cuts, the prosthesis is in a precise known location relative to the other skeletal member.

The same mounting holes provided for the guide to make the cuts to the skeletal member may also be used to mount a guide for drilling bore holes for mounting the prosthesis. In this way, a prosthesis having lugs depending from the back thereof is precisely positioned for mounting. By using the same mounting holes to drill the lug holes, the lug holes are placed in precise locations in order to mount the prosthesis relative to the joint in a precise known position.

The invention further includes the novel spacing mechanism which physically displaces the bones relative to one another in order to place them in the appropriate spacial relationship. This spacer may include means for attaching the positioner described above thus providing a single unit which has both the spacial, rotational and angular position of the skeletal members fixed.

DESCRIPTION OF THE PREFERRED EMBODIMENTS

The invention will now be described in connection with the accompanying drawings.

Figure 1:
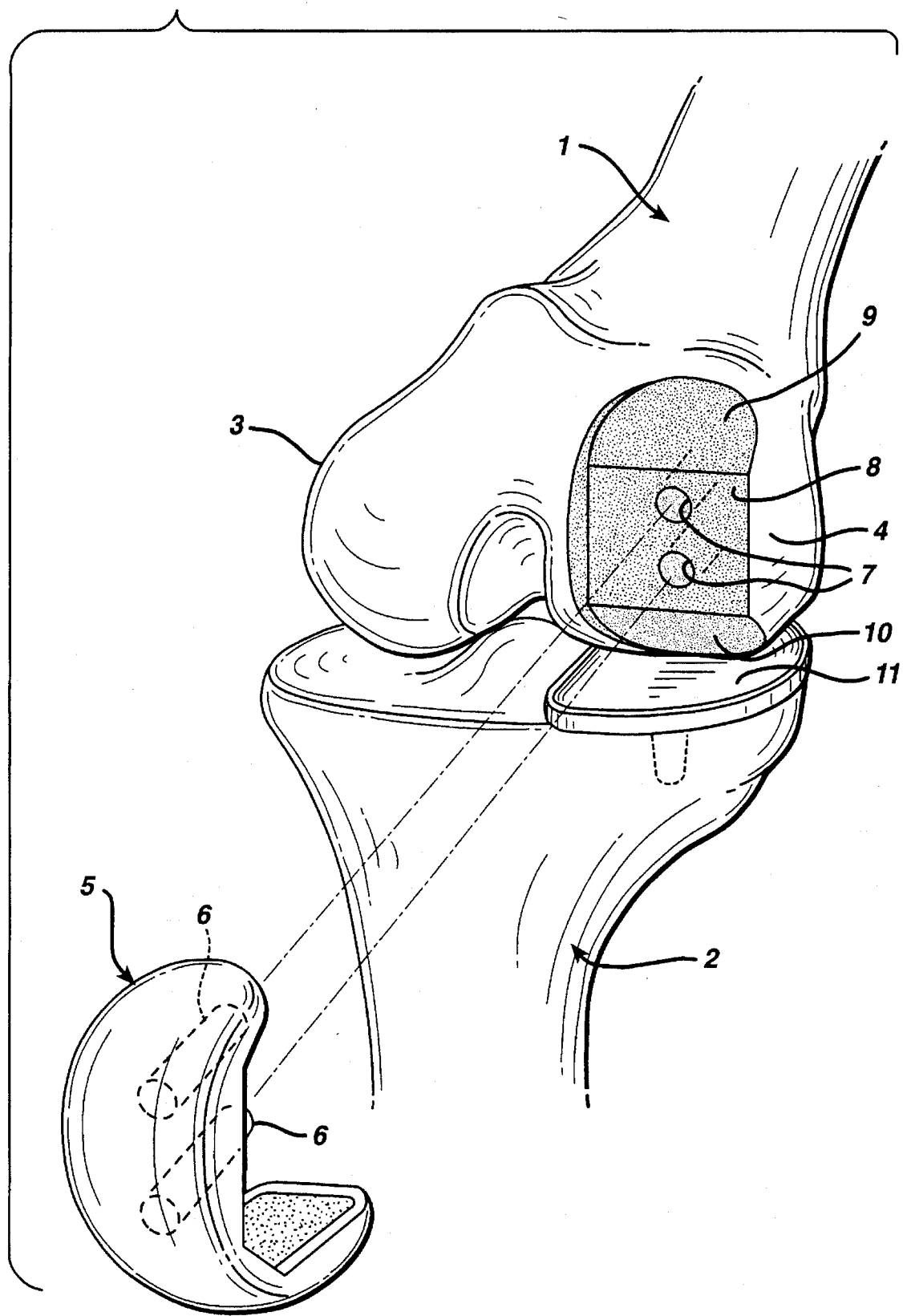
FIG. 1 shows the prepared distal femur and proximal tibia receiving the femoral portion of the knee prosthesis.

In FIG. 1, there is shown a femur 1 of a knee joint between that femur and the adjacent tibia 2. The femur has formed thereon naturally occurring condyles 3 and 4. Condyle 4 has already been prepared for reception of a prosthesis element 5. The prosthesis element is mounted on the femur through a frictional fit of lugs 6 and lug holes 7 formed in the distal portion of the femur after certain femoral cuts have been made. The femur has been shaped by providing a distal femoral cut 8 forming a substantially planer surface perpendicular to the mechanical axis of the femur. That is, perpendicular to the alignment along the central axis of the femur to the ball of the hip. There is provided an anterior chamfer 9 and a posterior chamfer 10 for reception of the prosthesis element 5 and the articulation of that prosthesis element relative to the tibia. The tibia has implanted thereon a tibial tray 11 which frictionally rides against the prosthesis element 5 after the replacement surgery has been performed.

Figure 2:
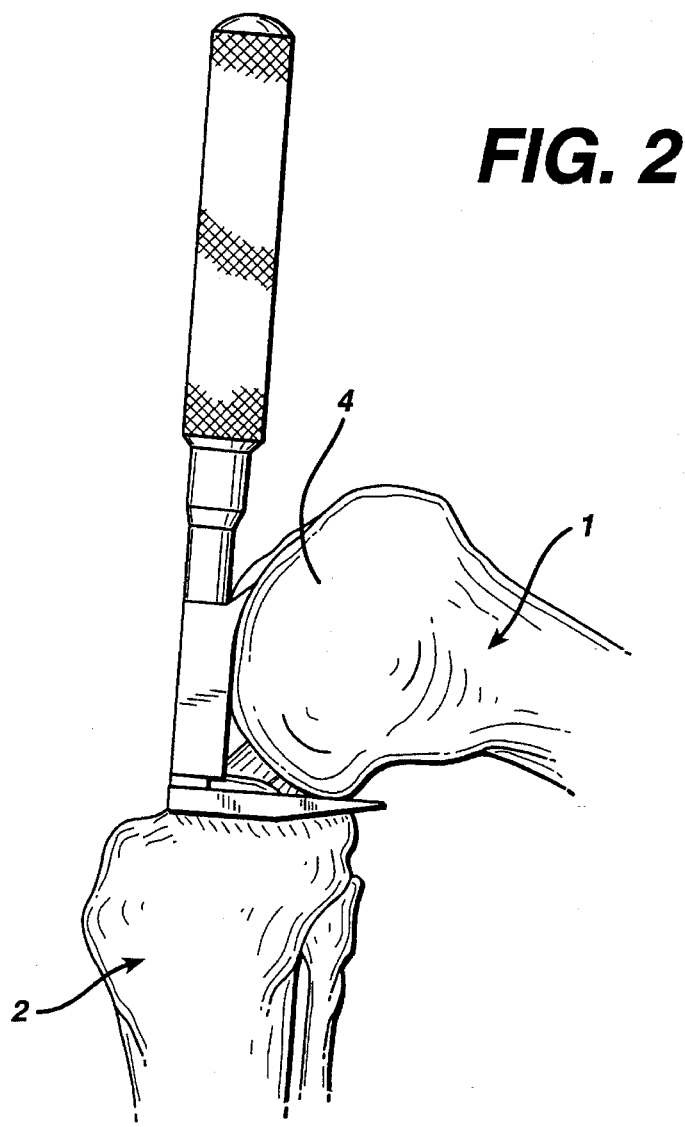
FIG. 2 shows a unique measuring device of the invention used to measure the distal femur prior to making the cuts in order to size the necessary prosthesis.
Figure 3:
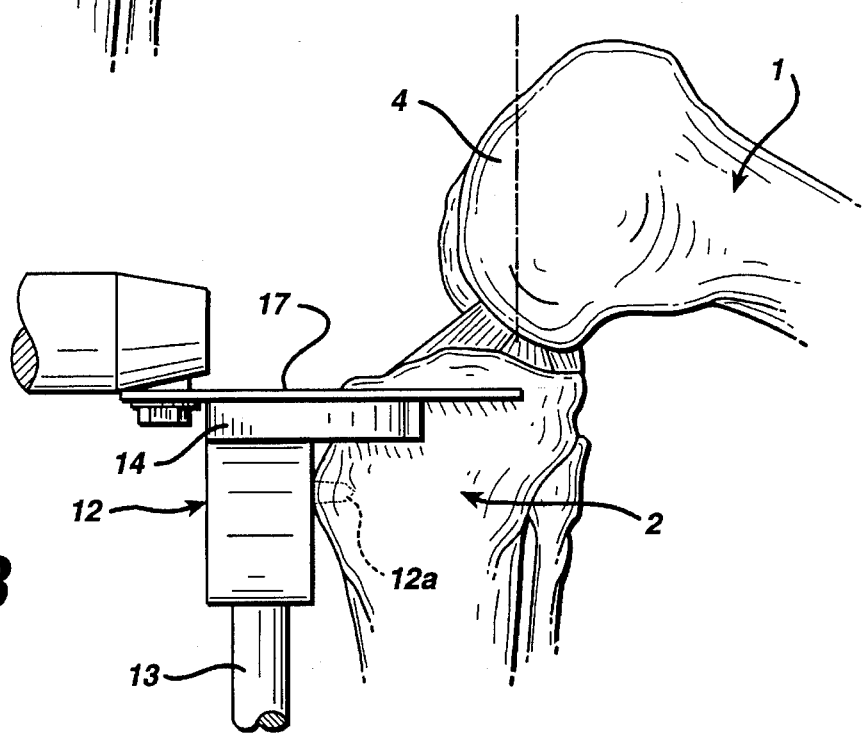
FIG. 3 shows the alignment device of the present invention attached to the proximal tibia while making the proximal tibial cut.
Figure 4:
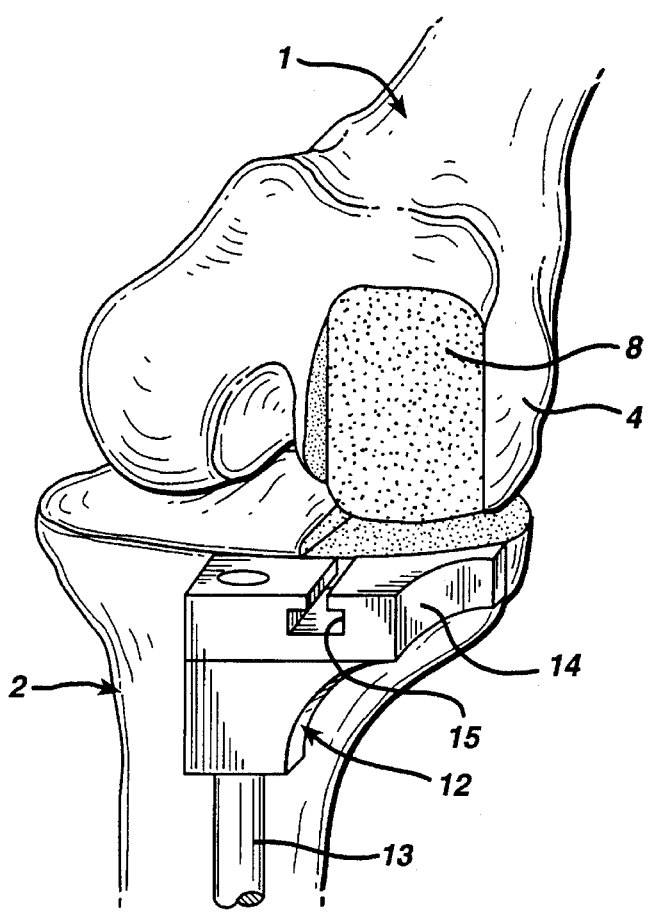
FIG. 4 shows the proximal tibial cut and the distal femoral cut already made.
Figure 5:
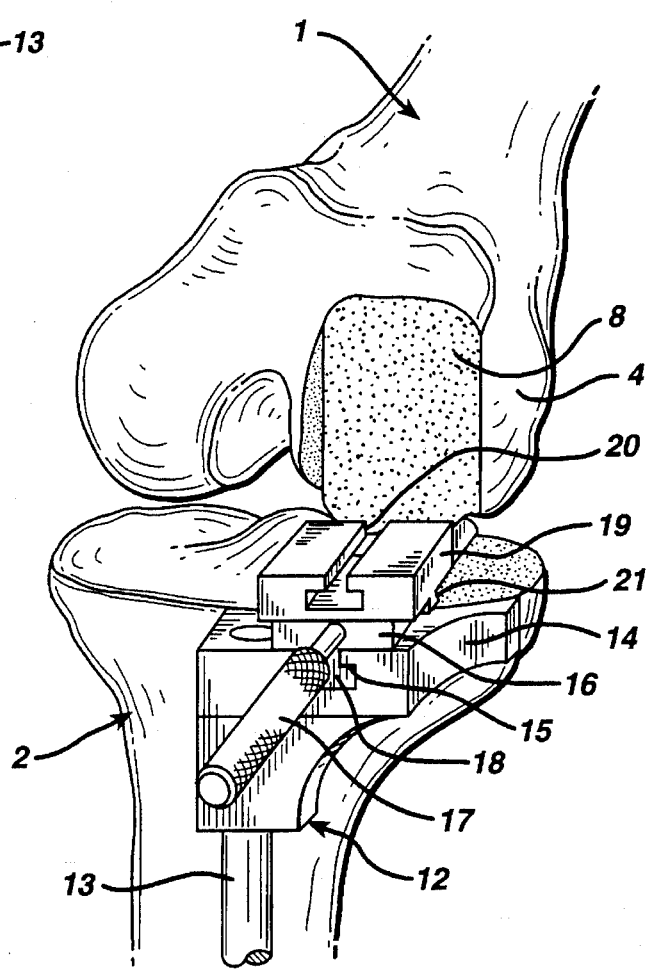
FIG. 5 shows the insertion of the mounting portion of the instrumentation of the present device onto the tibial portion of the instrumentation.

In order to provide appropriate cuts to the distal femur, the instrumentation of the present invention is used. Initially, as shown in FIG. 2, the diseased condyle is measured using a unique measuring device. This device is correlated in a known manner to a set of prostheses components of various sizes which correlate to the size measured by the instrumentation. That is, the distal femur is measured in order to find the appropriate prosthesis to replace the removed bone. As seen in FIG. 3, a tibial guide element 12 having an extended down rod 13 and a platform 14 is mounted to the tibia. The surgeon determines the appropriate depth of cut for the tibial osteotomy and mounts the tibial element by driving tapered pins 12a into the tibia at the appropriate height. The instrument is aligned with the tibia by extending the down rod 13 along the length of the tibia and aligning the end of the down rod with the ankle in an appropriate manner. This manner is easily determined by those of ordinary skill in the art. The platform 14 of the tibial guide acts as a saw guide for the saw blade 17 which is used to cut away the necessary bone on the proximal tibia. In a similar manner, a similar guide device to the tibial platform is mounted to the femur with the down rod aligned with the ball of the hip in order to provide the proper plane. This device guides a saw to make the appropriate distal femur cut 8 which cut is shown in FIG. 4. The tibial guide is formed of a sufficiently hard metal material such as stainless steel. The instrumentation is provided to mate specifically with either the medial or lateral portion of each of the left or right legs.

The distal femur cut and proximal tibial cut are made specifically with reference to the mechanical axis of the leg. However, the femur requires certain chamfer cuts and a posterior cut in order to fit the prostheses thereon. These cuts must be closely related to the position of the tibia and must take into account the thickness of the tibial tray to be implanted and the prostheses to be implanted.

Figure 6:
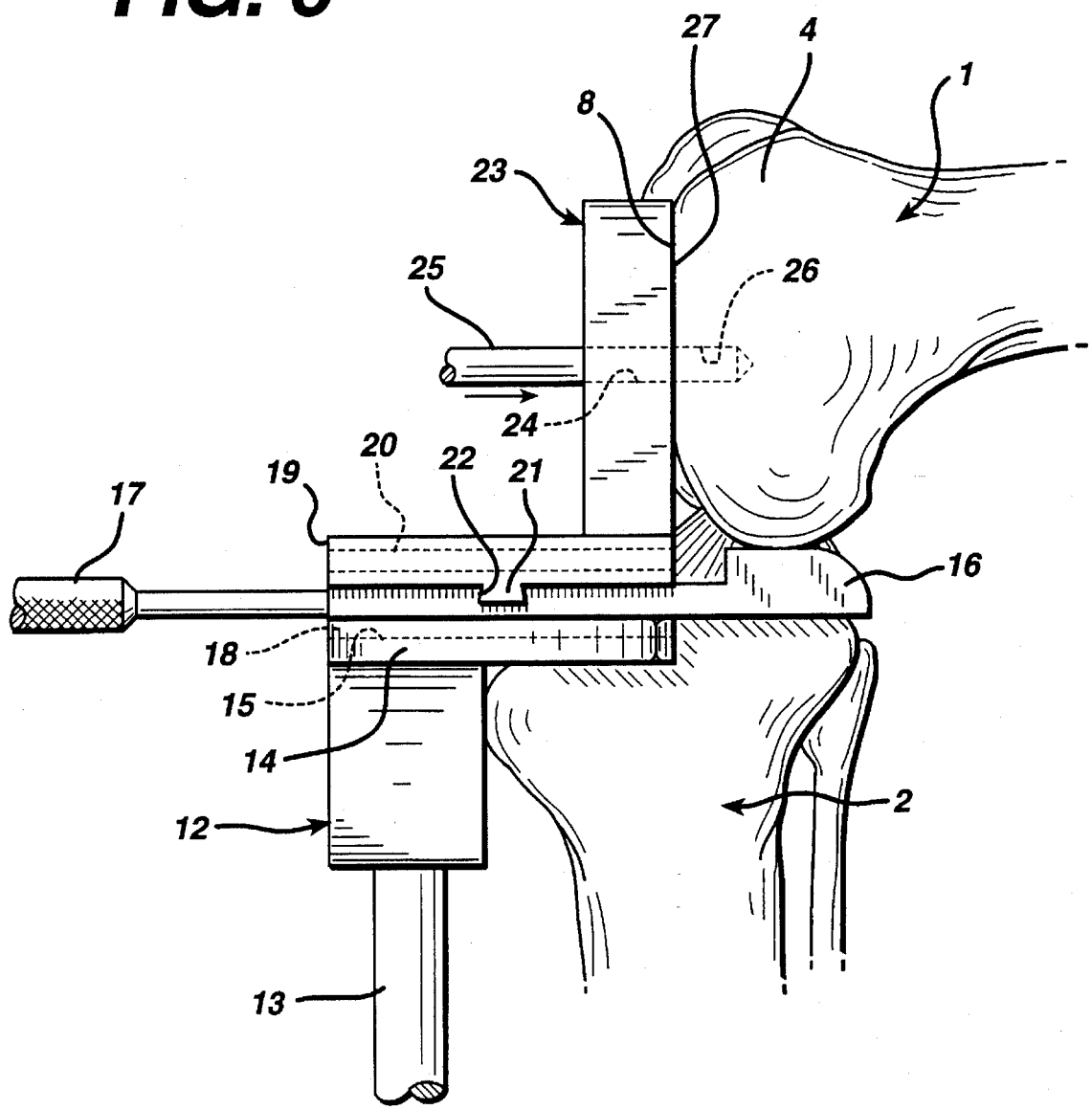
FIG. 6 is a side view showing the interrelationship between the femoral guide drill and the tibial portion of the instrumentation.
Figure 7:
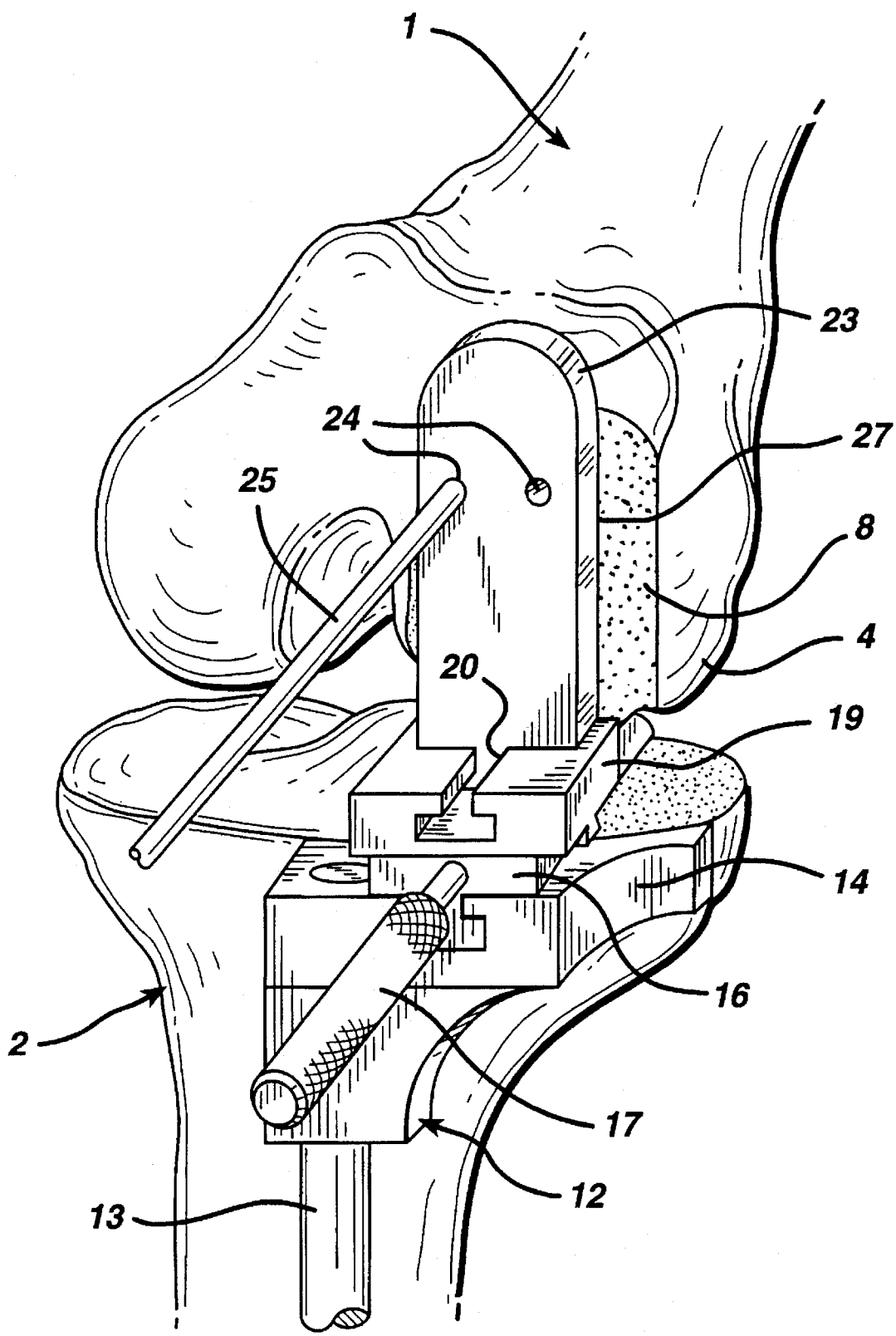
FIG. 7 is a perspective view of the operation being shown in FIG. 6.
Figure 8:
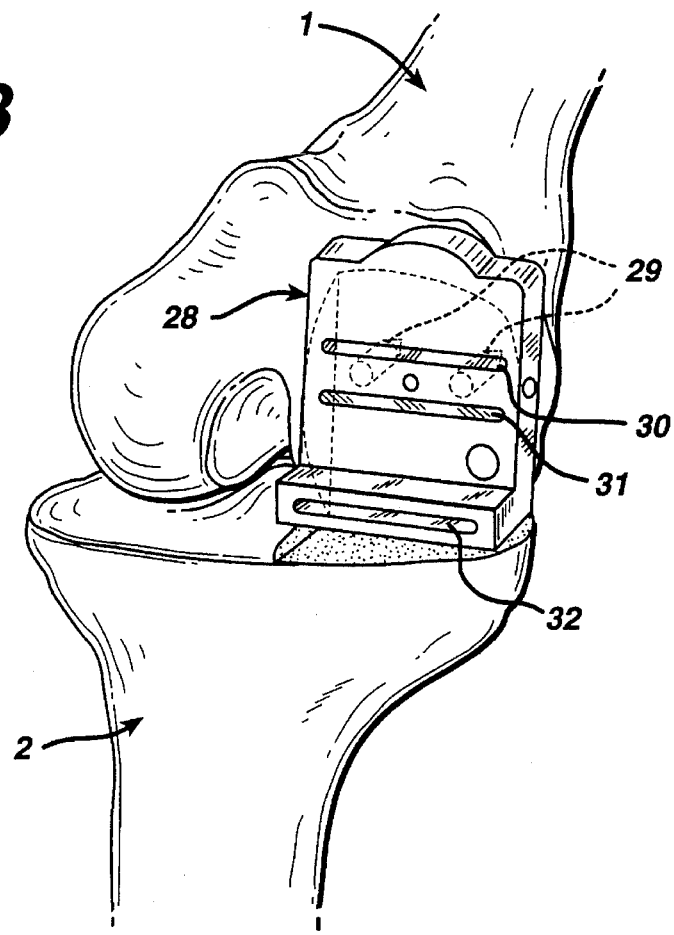
FIG. 8 is a perspective view showing the femoral saw guide mounted to the distal femur in the holes prepared in the operation depicted in FIGS. 6 and 7.
Figure 9:
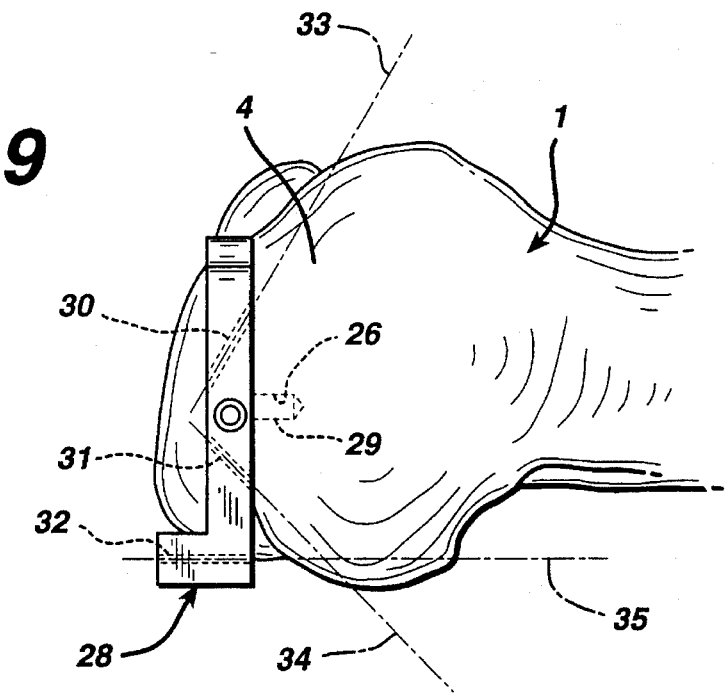
FIG. 9 is a side view of the instrumentation of FIG. 8.
Figure 10:
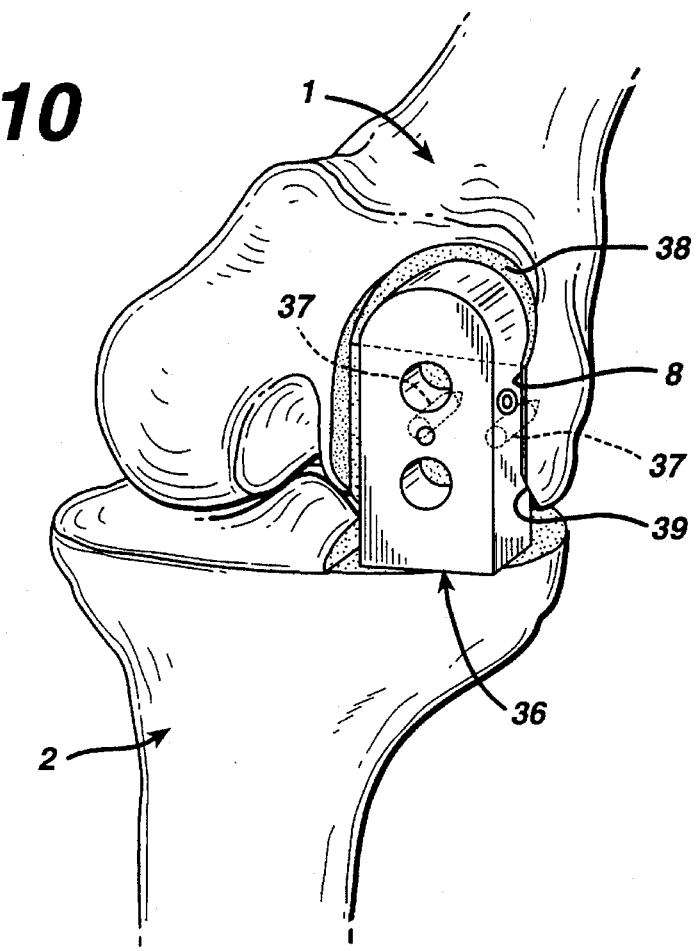
FIG. 10 shows a drill guide block mounted to the distal femur.
Figure 11:
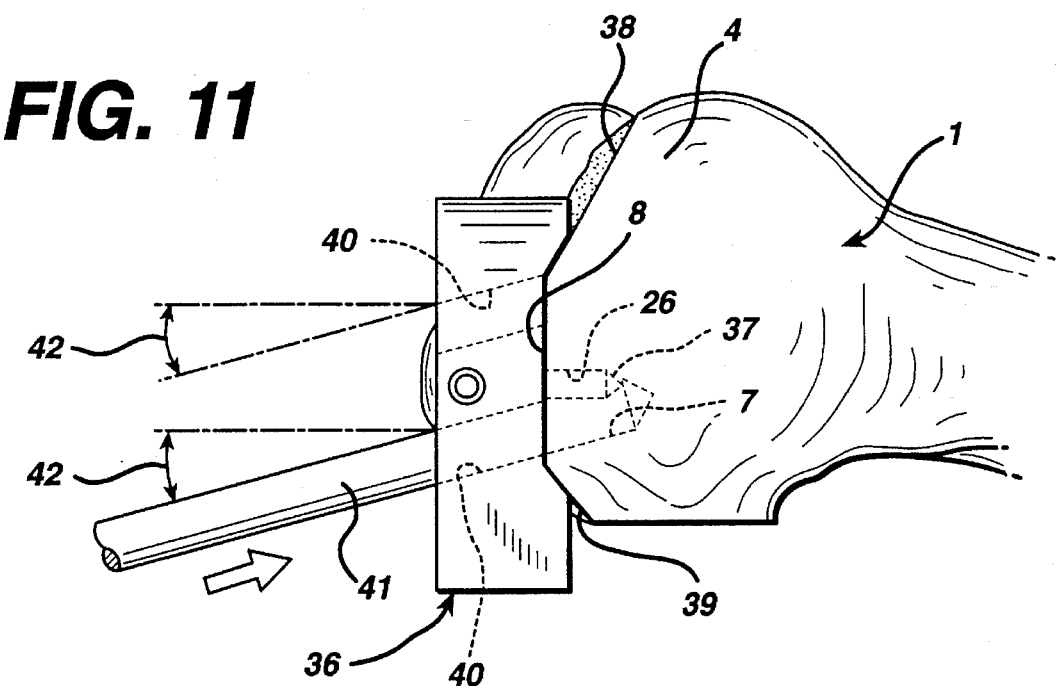
FIG. 11 shows the side view of the guide block in FIG. 10.

The tibial platform now provides a second function through the key slot 15 defined therein. A spacer element 16 having a handle 17 is inserted into the key slot via a tongue 18 formed thereon. The femur and tibia are placed in flexion and the spacer is positioned between the femur and tibia as shown in FIG. 6. This spacer is sized to provide appropriate tension to the ligaments of the knee joint and thus determine the size of the tibial tray and thickness of the prostheses necessary. This also places the femur and tibia in an appropriate separation for the next several steps of the surgical procedure. The spacer receives thereon a carriage 19 having a key slot 20 formed therein. The carriage 19 is received on the spacer via a dove-tail key 21 which fits in a dove-tail formed slot 22 in the spacer. As can be seen from the drawings, the dove-tail slot 22 runs perpendicular to the slot 15 defined in the platform. Thus, the spacer can be inserted from the anterior to the posterior direction of the tibia and force the femur into its separated position. The platform then moves in either from the medial or lateral side providing a positionable apparatus which can be moved forward and back by movement of the spacer and to the left or right via the interaction of the dove-tail 21 and the slot 22 defined by the spacer. The carriage 19 initially receives thereon a drill guide 23. The drill guide 23 has defined therein a pair of guide openings 24 which guide a drill 25 while making a mounting hole 26 in the distal end of the femur.

In use, the drill guide 23 has a face 27 at a known and predetermined angle to the platform 14. Actually, the known predetermined angle is with respect to the spacer 16 which is held in face-to-face alignment with the top of the platform. This face 27 is then placed adjacent the distal end of the femur, and the femur is positioned such that the original distal femur cut is in face-to-face engagement with the face 27 of the drill guide 23. Thus, prior to drilling, the femur and tibia are placed in spacial relationship by the spacer 16 and in angular relationship by the drill guide 23 through its face-to-face engagement between the surface 27 and the distal cut 8. Once the femur is positioned, the drill 25 is used to drill the mounting holes 26 in the distal cut of the femur. Having thus established the particular relationship between the mounting holes 26 and the distal femur cut 8 and the proximal tibia cut, the drill guide and spacer may be removed.

The femur has now been supplied with the mounting holes 26. These mounting holes receive a femoral saw guide 28 which is mounted therein through a frictional fit via lugs 29 projecting from the bottom side of the guide. The guide defines an anterior chamfer slot 30, a posterior chamfer slot 31 and a posterior femoral cut slot 32. These guides are used to position and orient the saw when making the anterior chamfer, the posterior chamfer and the posterior femoral cuts to the distal ends of the femur.

The anterior femoral cut is made along a plane 33 defined by the slot 30 and the posterior chamfer is made along a plane 34 defined by the slot 31. Finally, the posterior cut is made along a plane 35 which is defined by the slot 32.

After the anterior and posterior chamfers and the posterial femoral cut have been made, the saw guide 28 is removed and a prostheses lug hole drill guide 36 is mounted in the same mounting holes 26 via lugs 37 extending from the bottom of the drill guide. The drill guide has formed thereon a series of angular surfaces which mate with the posterior chamfer 38, the anterior chamfer 39 and the original distal femoral cut 8. Thus, the guide is placed in the proper position to make the openings for receiving the mounting lugs of the prosthesis. The drill guide defines a pair of openings 40 which are positioned and oriented to make openings specific to the prosthesis to be used. A drill 41 is used to drill out the openings and, in practice, the guide may be at an angle 42 to the actual mechanical axis of the femur. The drill defines the prosthesis mounting holes 7 and then the drill guide 36 is removed from its position adjacent the distal femur.

A prosthesis similar to that shown in FIG. 1 is then mounted on the distal femur by a frictional fit between the lugs 6 and the openings 7 formed by the drill. A tibial tray 11 is mounted in the cut formed on the proximal tibia and the surgical site is closed. The condyle prostheses and tibial tray may be mounted in any known manner. Therefore, the lugs 6 and openings 7 may merely provide an orientation function while the prostheses is held in place by other means.

It can easily be seen by one of ordinary skill in the art that minor departures from the specific function features and structures shown in this application can be made without escaping the spirit and scope of the invention which I have made.

What is claimed is:

1. A method of replacing a portion of a knee joint in an animal with an implanted prosthesis comprising:
    a. positioning a first guide relative the distal end of a femur and making a distal femoral cut using said guide;
    b. positioning a second guide adjacent a proximal end of a tibia and making a proximal tibial cut using said guide;
    c. attaching a spacer element to said second guide and positioning said spacer between said proximal tibia end and distal femur end to provide a spacing between said distal femur end and proximal tibial end when said femur and tibia are in flexion which correlates to the operative thickness of the implanted prosthesis;
    d. attaching a guide block having at least two guide bores to said spacer to form a predetermined angle between a guide face of said guide block and the proximal tibial cut;
    e. positioning said femur with said distal femoral cut adjacent to said guide face and matching said guide face with said spacer in place;
    f. boring at least two mounting bores in the distal femur using said guide bores in said guide block to position said mounting bores;
    g. mounting a chamfer cut guide to the distal end of the femur using said mounting bores to position the chamfer cut guide on the femur;
    h. cutting at least one femur chamfer cut using said chamfer cut guide to position said cut;
    i. attaching a femoral prostheses component along said at least one femur chamfer cut; and
    j. attaching a tibial prostheses component along said proximal tibia cut.

2. The method according to claim 1 further comprising mounting a lug bore guide to the distal end of the femur using said mounting bores to position the lug bore guide and boring at least one lug bore in the distal end of the femur using the lug bore guide to position the lug bore and positioning the said femoral prosthesis component on said femur at least in part by positioning a lug depending from said femoral prosthesis component within said lug bore.

3. The method according to claim 2 wherein three cuts are made to the distal end of the femur using said chamfer cut guide to guide each of the three cuts without removal or repositioning of the chamfer cut guide between cuts.

* * * * *